United States Patent [19]

McHugh

[11] 4,256,763

[45] Mar. 17, 1981

[54] TREATMENT OF HERPES SIMPLEX INFECTIONS AND ACNE

[76] Inventor: John E. McHugh, 4322 Hayvenhurst Ave., Encino, Calif. 91436

[21] Appl. No.: 943,811

[22] Filed: Sep. 19, 1978

[51] Int. Cl.³ ............................................. A61K 31/34
[52] U.S. Cl. .................................................. 424/285
[58] Field of Search ....................................... 424/285

[56] References Cited

U.S. PATENT DOCUMENTS

| | | | |
|---|---|---|---|
| 3,991,211 | 11/1976 | Cebrian | 424/338 |
| 4,046,918 | 9/1977 | Cebrian | 424/338 |
| 4,046,919 | 9/1977 | Cebrian | 424/331 |

FOREIGN PATENT DOCUMENTS 2130346 12/1971 Fed. Rep. of Germany .
2351512 4/1975 Fed. Rep. of Germany .
1383293 2/1975 United Kingdom .

OTHER PUBLICATIONS

Bauer et al., Chemotherapy of Virus Diseases, Section 61, vol. 1, Pergamon Press, pp. 262, 263, 278–281, 338–346, (1973).
Chemical Abstracts 76: 103763Z, (1972).
Chemical Abstracts 83: 84874T, (1975).

*Primary Examiner*—Leonard Schenkman
*Attorney, Agent, or Firm*—Lyon & Lyon

[57] ABSTRACT

There is disclosed a method of treating inflammatory viral infections, acne and dermatitis conditions comprising the administration of an effective dosage of 3,3-Bis(p-hydroxyphenyl)phthalide (phenolphthalein). The dosage may be administered orally or topically depending on the condition being treated.

11 Claims, No Drawings

TREATMENT OF HERPES SIMPLEX INFECTIONS AND ACNE

BACKGROUND OF THE INVENTION

This invention relates to the discovery that 3,3-Bis (p-hydroxyphenyl)phthalide is an effective treatment for certain inflammatory skin conditions, especially those of a viral origin. Phenolphthalein has long been known as one of a group of primary diphenylmethane cathartics. The cathartic effect of phenolphthalein was reportedly discovered in 1902 and since that time it has been widely employed in laxative formulas. It is also reported that phenolphthalein is relatively nontoxic. Goodman & Gillman, *Pharmacological Basis of Theraputics* (4 Ed. 1977) "Cathartics and Laxatives" pp. 1021 and 1022. Phenolphthalein is also used as an indicator in titrations of mineral and organic acids and most alkalies.

Although inflammatory viral infections may be caused by a wide variety of viruses, a common virus which produces persistently hard to treat conditions is the Herpes Simplex virus. Type I normally produces above waist infections while Type II produces lesions below the waist, in the genital region. Common manifestations of Herpes Simplex I infections are labialis (cold sores, fever blisters, etc.) pharyngitis, keratitis, skin infections (herpetic whitlow), encephalitis, and chronic ulcerative stomatitis. Herpes Simplex Type II may cause progenitalis oropharyngeal infections, meningitis and encephalitis. Other manifestations of inflammatory viral infections are canker sores, sun blisters and other such skin lesions and ulcerous conditions.

Inflammatory viral infections have proven very difficult to treat and in many instances are allowed to run their course with symptomatic treatment such as ointments, local anesthetics and the like. Treatment for Herpes Simplex infections includes dusting with bismuth formic iodide, application of camphor spirit, ephinephrine, idoxuridine, adenine arabinoside, large doses of steroids and X-ray or grenz ray therapy.

Inflammatory skin conditions (dermatitis) which occur frequently include photodermatitis and actinic dermatitis such as sunburn, actinic karatosis and the like, eczema, pruritus, acute and chronic lesions, burning, swelling and blistering. These conditions are also difficult to treat with moisturizing creams, lotions and other topical agents being employed.

Acne is a disease of the pilosebaceous unit which includes the hair follicle and its sebaceous gland. They are most numerous on the face but also are found in abundance on the back, chest and upper arms. (L. Kaminester, "Acne," *Journal of the American Medical Association*, May 19, 1978, Volume 239, No. 20, pages 2171-72) Normally the sebaceous glands secrete an oily material called sebum which rises to the top of the hair follicle and then flows out onto the skin surface. Acne occurs when the canals through which the oily sebum flows become plugged up. Bacteria, chiefly *Corynebacterium acnes*, live in the hair follicles and break down complex fats into triglycerides and free fatty acids.

The plugged hair follicles, or comedo, often ruptures into the lower skin areas and dumps free fatty acids, horn, fat, hair and bacterial products into the dermis, creating a "toxic" foreign body response which can cause scarring. Recently recommended treatment of acne includes oral antibiotics that effectively decrease the bacterial count of *C acnes*. These include tetracycline and erythromycin which selectively concentrate around the hair follicles, thus reducing the *C acnes* count and subsequent inflammation. Those antibiotics may also be applied in topical application. Kaminester reports that topical applications of antibiotics are inferior to orally administered antibiotics and should not be used in severe cases of inflammatory acne. Topical tretinoin and benzoyl peroxide preparations have also had beneficial effects.

It is an object of the present invention to provide a fast acting, effective treatment of inflammatory viral infections.

It is a further object to provide a topical agent to arrest dermatitis conditions.

It is yet a further object of the invention to provide a topical agent which reducts the *C acne* count in hair follicles and thereby helps prevent and aids in curing acne.

SUMMARY OF THE INVENTION

The method of the invention provides for the treatment of inflammatory viral infections by the administration of an effective oral or topical dosage of phenolphthalein. The orally administered dose is preferably about 15 to about 30 milligrams of phenolphthalein administered every 8 hours to treat inflammatory viral infections including Herpes Simplex I and II infections, canker sores, cold sores and sun blisters. Although higher dosages, for example up to about 100 milligrams, of the oral preparation are effective against inflammatory viral infections, the preferred dosages are selected to avoid the laxative effect of the phenolphthalein. The phenolphthalein may advantageously be formulated with other drugs to provide relief from symptoms associated with the disease being treated.

Phenolphthalein may also be applied as a topical agent within the scope of the invention to relieve or cure Herpes Labialis, cold sores, sun blisters, canker sores, photodermatitis, actinic dermatitis, actinic keratosis and dermatitis manifested as pruritus, acute and chronic lesions, burning, swelling, and blistering. When applied as a topical agent phenolphthalein is mixed with a suitable carrier and may be formulated to provide a moisturizing cream with anti-viral action.

In a topical preparation including antibiotics, phenolphthalein may be applied to effectively treat acne. In such applications the suitable carrier will be selected to avoid comedogenic agents.

DETAILED DESCRIPTION

In an informal clinical study 41 patients with symptoms of Herpes Labialis were treated with oral dosages of phenolphthalein. The patients were treated at different times over a period of about two months. The initial dosage was one hundred milligrams administered every 8 hours for the first day and every 12 hours thereafter. Due to complaints related to the laxative effect of the phenolphthalein, the dosage was reduced to 30 milligrams in the early stages of the testing. Of the 41 patients treated, 39 made complete recovery within two days without any noticeable development of the cold sore. The other two patients made complete recovery with no swelling or visible evidence of the cold sore remaining after three days. A control group of 24 patients with Herpes Labialis history were selected at random from clinical files as a control group. Of the 24 patients, 5 were excluded because of the total absence of early indications of infection. The other 19 patients were treated conventionally over a 10 day period. Only 4 experienced even partial relief from developing cold sores and 15 developed active cold sores and blisters which lasted up to 4 weeks.

Follow-up observations on the 41 patients treated with phenolphthalein disclosed no development of Herpes Labialis. The results of this informal study indicate that phenolphthalein is a very effective drug for preventing and arresting the development of cold sores and blisters at the time of initial appearance in patients.

Oral dosages of phenolphthalein have been successfully administered to victims of Herpes Simplex infections, including cold sores, fever blisters and Herpes Genitalis. Oral dosages have also proved effective to relieve and cure canker sores within a matter of hours.

Phenolphthalein has successfully been combined with agents to relieve other cold and flu symptoms often associated with inflammatory viral infections. Tablets were prepared for this purpose having the ingredients listed in Table 1. In some formulations the phenolphthalein content was one hundred milligrams but this amount was reduced to thirt milligrams because of complaints of the laxative effect. Other formulations comprising antihistamines, decongestants, analgesics and antipyretics will be readily apparent to those skilled in the art and may be selected for specific conditions to be treated.

TABLE I

| Ingredient | Nominal Amount | Analyzed Amount |
|---|---|---|
| Phenolphthalein | 30 mg. | 27.6 mg. |
| Acetaminophen | 325 mg. | 316. mg. |
| Caffeine | 33 mg. | 36.1 mg. |
| Chlorpheniramine Maleate | 2 mg. | 1.9 mg. |
| Phenylephrine HCI | 10 mg. | 9.7 mg. |

The inventor has been contacted by more than 20 men and women who indicated they were Herpes Simplex sufferers and that they received relief from cold sores and other Herpes Simplex inflammations by taking the tablets. The recommended dosage is one tablet every eight hours for the first day followed by one tablet every twelve hours until symptoms disappear. One person reported that she was a cold sore sufferer for years and that her ingestion of tablets, having either 30 or 100 milligrams of phenolphthalein with the remainder of the ingredients as set forth in Table 1, provided satisfactory results in combating cold sores.

A male who used tablets having the composition set forth in Table 1 reported that he had suffered from diagnosed Herpes Simplex II since 1972. He reported he took the recommended dosages and that the development of Herpes Simplex II was haulted.

Phenolphthalein has also been prepared for topical application by formulating it at a concentration of 250 mg. per ounce with Natural Callagen Protein with provitamin D-panthenol, lecithin and allantoin. The topical formulation provided a moisturizing cream which was effective in treating dermatitis conditions including photodermatitis, actinic dermatitis, actinic karatosis, eczema, pruritus, acute and chronic lesions, burning, swelling, blistering and acne.

Phenolphthalein was formulated at the same concentration in a topical ointment with benzoyl peroxide and calamine base and demonstrated to be effective in providing relief from acne vulgaris and acne conglobate.

In treating dermatitis conditions one formulation included 500 milligrams of phenolphthalein combined with 2 ounces of a moisturizing skin cream containing purified water (USP), Vitamin E, polyoxyethylene monostearate, glyceraol monostearate, propylene glycol, cetyl alcohol, stearyl alcohol and parabens. That topical preparation was effective in promoting quick healing and growth of new skin in the treatment of rashes, blemishes and skin lesions commonly associated with old age.

As will be readily appreciated by those skilled in the art, phenolphthalein for oral application may be formulated with a variety of other agents to treat disease conditions associated with the disease for which phenolphthalein is selected. While orally administered phenolphthalein is effective in dosages at least up to 100 milligrams, the preferred dosage is from about 15–30 milligrams in order to avoid the objectionable laxative effect. The oral dosage may be administered in tablet, suspension or solution form.

In preparing topical applications for the treatment of dermatitis conditions or acne it is within the scope of the invention to formulate phenolphthalein with suitable carriers to aid in the application on and absorption into the effected area. Such carriers are well known to those skilled in the art. In topical applications the concentration of the phenolphthalein in the carrier may vary widely. For example 500 mg. in 2 ounces of carrier is effective against acne. It is believed that a concentration of at least about 250 mg. per ounce of carrier will be effective. However, the scope of the invention includes all effective concentrations.

While specific formulations have been given above it is not intended that they limit the scope of the invention. The invention is limited only by the scope of the appended claims set forth below.

I claim:

1. The method of treating Herpes Simplex viral infections and acne in humans comprising the administration of an effective dosage of 3,3-Bis(p-hydroxyphenyl)phthalide to a person afflicted with at least one of said conditions.

2. The method of claim 1 wherein the dosage is administered orally.

3. The method of claim 1 wherein the dosage is administered topically to an externally accessible portion of the afflicted person's body, which portion is affected by at least one of said conditions.

4. The method of claim 2 wherein said dosage comprises from about 15 to about 100 milligrams of 3,3-Bis(p-hydroxyphenyl)phthalide.

5. The method of claim 2 wherein said dosage comprises from about 15 to about 30 milligrams of 3,3-Bis(p-hydroxyphenyl)phthalide.

6. The method of claim 3 wherein the dosage of 3,3-Bis(p-hydroxyphenyl)phthalide is suspended in a carrier.

7. The method of claim 3 wherein the condition being treated is acne.

8. The method of claim 7 wherein the condition being treated is acne and the compound 3,3-bis(p-hydroxyphenyl)phthalide is suspended in a carrier which is noncomedogenic.

9. The method of claim 8 wherein benzoyl peroxide is also suspended in the carrier.

10. The method of claim 1, 2, 4 or 5 wherein the dosage of 3,3-Bis(p-hydroxyphenyl)phthalide is combined with an effective dosage of an antihistamine, a decongestant, an analgesic, an antipyretic or mixtures thereof.

11. The method of claim 10 wherein said dosage of 3,3-Bis(p-hydroxyphenyl)phthalide is combined with acetaminophen, chlorpheniramine maleate and phenylephrine HCI.

* * * * *